United States Patent
Huttner et al.

(10) Patent No.: US 8,756,731 B1
(45) Date of Patent: Jun. 24, 2014

(54) PHOTOTHERAPY INFANT SWADDLING BLANKET

(71) Applicant: Bionix Development Corporation, Toledo, OH (US)

(72) Inventors: James Huttner, Sylvania, OH (US); Susan Brangham, Temperance, MI (US)

(73) Assignee: Bionix Development Corporation, Toledo, OH (US)

( * ) Notice: Subject to any disclaimer, the term of this patent is extended or adjusted under 35 U.S.C. 154(b) by 0 days.

(21) Appl. No.: 13/864,309

(22) Filed: Apr. 17, 2013

Related U.S. Application Data (60) Provisional application No. 61/625,268, filed on Apr. 17, 2012.

(51) Int. Cl.
    *A47G 9/02* (2006.01)
    *A41B 13/06* (2006.01)

(52) U.S. Cl.
    CPC ..................................... *A41B 13/06* (2013.01)
    USPC ............... 5/494; 5/601; 5/603; 5/655; 2/69.5

(58) Field of Classification Search
    CPC ..... A47D 15/00; A47D 15/008; A47D 15/02; A41B 13/06; A41B 13/065
    USPC .......................... 5/601, 603, 494, 655; 2/69.5
    See application file for complete search history.

(56) References Cited

U.S. PATENT DOCUMENTS

| | | | | |
|---|---|---|---|---|
| 2,803,824 A * | 8/1957 | Parish | | 2/69.5 |
| 3,034,132 A * | 5/1962 | Landsberger et al. | | 2/69.5 |
| 4,739,529 A * | 4/1988 | Mills | | 5/413 R |
| 4,897,885 A * | 2/1990 | Lunt | | 2/69.5 |
| 5,233,714 A * | 8/1993 | De Bell Daniel | | 5/655 |
| 5,792,214 A * | 8/1998 | Larsson et al. | | 607/88 |
| 6,253,380 B1 | 7/2001 | Larsson | | |
| 6,269,502 B1 * | 8/2001 | Exstrom | | 5/655 |
| 6,640,340 B2 * | 11/2003 | Gibson | | 2/69.5 |
| 6,662,390 B1 * | 12/2003 | Berger | | 5/486 |
| 6,839,924 B2 * | 1/2005 | Sims | | 5/494 |
| 6,868,566 B2 | 3/2005 | Gatten | | |
| 6,948,200 B2 * | 9/2005 | Wyman | | 5/494 |
| 7,043,783 B2 | 5/2006 | Gatten | | |
| 7,181,789 B2 | 2/2007 | Gatten | | |
| 7,340,842 B2 * | 3/2008 | Rabe | | 33/512 |
| 7,603,732 B2 * | 10/2009 | Robles et al. | | 5/655 |
| 7,673,354 B2 * | 3/2010 | Fader | | 5/494 |
| 8,302,225 B1 * | 11/2012 | Earnest | | 5/494 |
| 8,347,432 B2 * | 1/2013 | Schmid et al. | | 5/494 |
| 8,365,325 B2 * | 2/2013 | Schneider | | 5/494 |
| 8,539,620 B1 * | 9/2013 | Wynh | | 5/494 |
| 2006/0010600 A1 * | 1/2006 | Kendy | | 5/482 |
| 2008/0116401 A1 | 5/2008 | Rice | | |
| 2008/0120774 A1 * | 5/2008 | Hite | | 5/494 |

(Continued)

*Primary Examiner* — Robert G Santos
*Assistant Examiner* — David E Sosnowski
(74) *Attorney, Agent, or Firm* — Marshall & Melhorn, LLC (57) ABSTRACT

A swaddling blanket comprises a continuous sheet of fabric material having a generally "T"-shaped configuration and being substantially light-transmissive for light having a wavelength in the range of 350 nm to 500 nm. An infant undergoing a course of phototherapy is swaddled in the sheet of fabric material so that the infant is snugly wrapped in the sheet of fabric material, the sheet of fabric material limiting arm and leg movement of the infant, with only a single layer of the sheet of fabric material between a phototherapy lamp and the infant.

7 Claims, 5 Drawing Sheets

(56) References Cited

U.S. PATENT DOCUMENTS

| | | | |
|---|---|---|---|
| 2010/0218314 A1* | 9/2010 | Mulheron | 5/494 |
| 2011/0231993 A1* | 9/2011 | Schmid et al. | 5/494 |
| 2013/0302555 A1* | 11/2013 | Dunn et al. | 428/78 |
| 2014/0020177 A1* | 1/2014 | Coates | 5/494 |
| 2014/0033430 A1* | 2/2014 | Daugherty et al. | 5/494 |

\* cited by examiner

PHOTOTHERAPY INFANT SWADDLING BLANKET

CROSS-REFERENCE TO RELATED APPLICATIONS

This application is claiming the benefit, under 35 U.S.C. §119(e), of the provisional application filed Apr. 17, 2012 under 35 U.S.C. §111(b), which was granted Ser. No. 61/625,268. This provisional application is hereby incorporated by reference in its entirety.

BACKGROUND OF THE INVENTION

Jaundice is a common condition in newborns, and refers to the yellow color of the skin and whites of the eyes caused by an excess of bilirubin in the blood. Bilirubin is produced by the normal breakdown of hemoglobin from red blood cells. Normally, bilirubin is metabolized and conjugated in the liver and is excreted as bile through the intestines. Jaundice occurs when bilirubin levels build up faster than a newborn's liver can break it down and pass it from the body.

Physiological (normal) jaundice occurs in most newborns. This mild jaundice is due to the immaturity of the baby's liver, which leads to a slow processing of bilirubin. It generally appears at 2 to 4 days of age and disappears by 1 to 2 weeks of age, and does not need treatment. Breastfeeding jaundice can occur when a breastfeeding baby is not getting enough breast milk because of difficulty with breastfeeding or because the mother's milk isn't in yet. This is not caused by a problem with the breast milk itself, but by the baby not getting enough to drink. Breastfeeding jaundice also appears in the first few days of life. Jaundice of prematurity occurs frequently in premature babies since they are even less ready to excrete bilirubin effectively. Jaundice in premature babies needs to be treated at a lower bilirubin level than in full term babies in order to avoid complications.

Pathologic (abnormal) jaundice can lead to a faster and higher rise of bilirubin levels. Causes of pathologic jaundice are many. Increased hemolysis, from ABO blood type incompatibilities, RBC membrane defects, and RBC enzyme defects, resolving cephaihematomas, maternal-fetal transfusion, and sepsis can result in high bilirubin levels. Pathologic jaundice can also result from a defect in the newborn liver preventing proper conjugation and excretion. Examples of this are decreased enzyme activity with prematurity, breast milk jaundice, hypothyroidism, and metabolic diseases. Finally, impaired excretion can occur from TORCH infections, severe metabolic disease, and hepato-biliary atresia, and can result in extremely high levels of bilirubin.

High levels of bilirubin—usually above 25 mg—can cause deafness, cerebral palsy, or other forms of brain damage in some babies, a condition called kernicterus. Because of this, the American Academy of Pediatrics recommends that all infants should be examined for jaundice within a few days of birth. Evaluation is done by simple blood test or, more recently, a transcutaneous bilirubin test device. If elevated bilirubin levels are found, they are plotted on a graph which correlates the infant's age (in hours) to the bilirubin level to determine the severity of the condition. When bilirubin levels are found to be in the range that warrants concern, treatment is begun.

The mainstay of treatment of hyperbilirubinemia is phototherapy. Phototherapy exposes the jaundiced infant to a bright blue-white light that creates bilirubin photoisomers in the skin of the patient. Normally, un-conjugated bilirubin is poorly water soluble and is mostly excreted through the bile, with only a small amount being excreted into the urine. Photo-isomerized bilirubin, however, is much more water soluble, and is readily excreted by the kidneys into the urine.

The efficacy of phototherapy relies on a combination of intensity and duration. Since only the skin under the phototherapy light can contribute to the photoisomerism, it is important that the child be as undressed as possible during the procedure. This usually translates into only diapers (for hygiene) and eye-shields (for safety).

A problem is that many infants, particularly premature infants also receiving other treatments such as nasal CPAP, are often restless during the phototherapy process and do not lay still. This causes undue stress on the infant, and can lead to increase respiratory and heart rates, increase energy expenditure, over-heating, and discomfort. A simple technique used in the nursery to calm irritable infants is swaddling, which is a method of snugly wrapping the infant in a blanket. The snug wrap comforts and quiets the infant without the need for medication. However, swaddling is not currently an option in infants undergoing a course of phototherapy because the blankets currently used would block most or all of the phototherapy light from reaching the infant's skin, rendering the phototherapy procedure ineffective.

Larsson, et al (U.S. Pat. No. 6,253,380) describes a restraining garment for an infant receiving phototherapy, said garment being comprised of a generally rectangular blanket with a pouch sized to receive an infant being disposed on its surface, and having a bottom surface substantially transparent to phototherapy light. In practice, the infant is placed in the pouch, and the entire garment placed over a phototherapy lamp. The infant thus receives phototherapy by illumination from below through the substantially transparent garment. There are significant problems with this approach. First, phototherapy lamps commonly available and in use in most nurseries are designed to rest above the infant and deliver illumination from above. There is no practical way to alter or re-configure these lights to provide illumination from below the infant, thus the device disclosed by Larrson would require the use of a new and specifically designed phototherapy lamp. Second, the garment described by Larrson discloses a simple pouch for holding the infant, with additional arms in said pouch for receiving the arms of the infant. Although this would be sufficient to restrain the infant's movement, such a garment would not provide the snug restraint needed for swaddling and thus would do little or nothing to comfort an infant undergoing a course of phototherapy for hyperbilirubinemia.

Rice (US 2008/0116401) discloses a method and apparatus for stabilizing a subject undergoing phototherapy treatment. In her patent application, Rice discloses a garment that is substantially transparent to phototherapy light and a method wherein an infant requiring phototherapy for hyperbilirubinemia is wrapped or clothed in said garment prior to the delivery of phototherapy. It is understood that the garment described in the Rice application may take several forms, including a blanket, a hat, or other suitable garment.

The Rice application does not specifically refer to the use of a blanket-like garment for swaddling and thereby comforting an infant receiving phototherapy. However, one skilled in the art will realize that the square or rectangular blanket in the Rice application can be used for such purpose. A problem, however, with the use of a simple square or rectangular blanket for swaddling an infant is that it will necessarily require the blanket to be wrapped more than once around the infant to provide a tight and securely snug wrap. This will result in at least two and perhaps multiple layers of fabric lying between the phototherapy lamp and the infant's skin. Unless the fabric material used in the construction of the garment disclosed by Rice is 100% transparent to the phototherapy light, each layer of fabric interposed between the infant and the phototherapy lamp will diminish the intensity of the phototherapy energy and reduce the effectiveness of the treatment. Multiple layers of fabric could potentially degrade the phototherapy energy to the point where the treatment is unduly prolonged or becomes ineffectual. No mention is made in the Rice application as to how to remedy this problem.

There are multiple patents describing blankets intended to swaddle an infant. Representative of these designs are those disclosed by Gatten (U.S. Pat. No. 7,181,789; U.S. Pat. No. 7,043,783; and U.S. Pat. No. 6,868,566). Gatten discloses an infant swaddling blanket formed from a continuous piece of material and having two arms. One blanket arm is just long enough to wrap once over an infant and be tucked partially beneath the infant. The other blanket arm extends from the opposite side of the back panel and is long enough to wrap around the infant more than once. It is recognized that a swaddling blanket of this construction would intersperse multiple layers of material between the infant and the phototherapy light and would significantly degrade the efficacy of the phototherapy treatment, possibly rendering it ineffectual. Thus, a swaddling blanket as disclosed by Gatten could not be used for swaddling an infant receiving phototherapy.

SUMMARY OF THE INVENTION

The current invention seeks to remedy the problems in the prior art by providing a swaddling blanket or wrap made of light-transmissive material. Using a blanket made of such material the irritable infant could be swaddled and comforted, while at the same time allowing the unimpeded delivery of phototherapy to the infant's skin. A further aim of this invention is to provide a garment that could be worn by infants undergoing a course of phototherapy to provide them warmth and comfort without impeding the delivery of the phototherapy.

The swaddling blanket comprises a continuous sheet of fabric material having a generally "T"-shaped configuration having a base region extending perpendicularly from a central portion of a cross region. The fabric material comprising the swaddling blanket is substantially light-transmissive for light having a wavelength in the range of 350 nm to 500 nm.

In accordance with the method of the invention for swaddling an infant undergoing a course of phototherapy, a sheet of fabric material that is substantially light-transmissive for light in the range of 350 nm to 500 nm wavelengths is provided, and the sheet of fabric material is folded or wrapped about the infant so that the infant is snugly wrapped in the sheet of fabric material, the sheet of fabric material limiting arm and leg movement of the infant, with only a single layer of the sheet of fabric material between a phototherapy lamp and the infant.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE INVENTION

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

The invention is a swaddling blanket for an infant undergoing a course of phototherapy for jaundice that does not impede the delivery of that phototherapy. The swaddling blanket is comprised of a continuous piece of fabric having a generally "T"-shaped configuration with a base region extending perpendicularly from a central portion of a cross region, the fabric having the properties of being >45% light-transmissive, and preferably >90% light-transmissive, for light in the range of 350 nm to 500 nm wavelengths. In a preferred embodiment of the device, the fabric consists of spun-bond polypropylene material having a weight of 10 to 15 grams per square meter (gsm).

The swaddling blanket of the current invention discloses a unique functional design that is intended to ensure that there is ever only a single layer of material interspersed between the phototherapy lamp and the infant receiving phototherapy.

Figure 1:
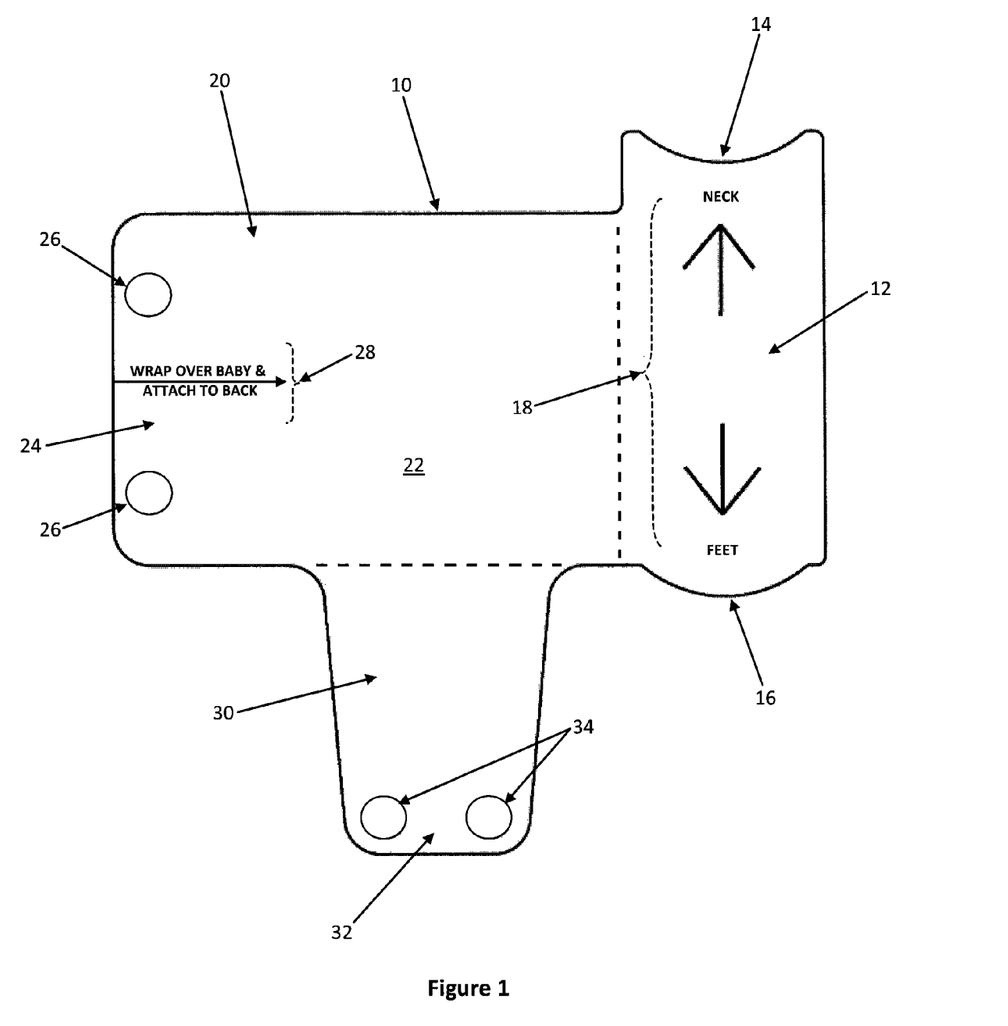
FIG. 1 is a plan view of a first embodiment of a phototherapy infant swaddling blanket in accordance with the invention.

In a first embodiment illustrated in FIG. 1, the swaddling blanket 10 formed with the generally T-shaped configuration defines three general regions (the dotted lines in the figures generally denoting this regions), said regions being continuous with each other. The first general region 12 is intended to be disposed behind the infant, having a cephalad or head end 14 and a caudal or foot end 16, such that in use the infant lies supine with his/her back resting over this region and head and feet oriented properly. As shown in FIG. 1, the head and foot ends 14, 16 define curved borders intended to mark proper head and foot placement of the infant atop the device, however such curved borders are optional, and alternately shaped borders are within the scope of the invention. Further, as shown in FIG. 1, markings 18 may be printed on the material that show patient head and foot placement/orientation. These markings are optional and may change or be omitted on alternate designs of the device.

The second general region 20 comprises an elongated arm that extends generally perpendicular to the first region and can act as a torso wrap portion. Thus, this second region 20 is intended to wrap over and around the infant with sufficient length to reach the infant's back, preferably to the approximate midpoint of the infant's back, but not long enough to wrap further around the infant. The center portion 22 of this second region 20 will lie generally atop the infant's torso when properly positioned, in a fashion that ensures that only a single layer of material is ever interspersed between the phototherapy lamp and the infant receiving phototherapy. A means of affixing the distal end 24 of this second region to the underside of the first region 12 may be included; said affixing means 26 is intended to provide the snugness required to swaddle an infant without the need to wrap multiple times around the infant and interfere with the phototherapy energy delivered. In the illustrated preferred embodiment of the device, said affixing means 26 is one or more tabs of Velcro-type hook material, although it is recognized that other means such as adhesive tapes may be used as well. Further, as shown in FIG. 1, markings 28 may be printed on the material that show wrapping directions. These markings are optional and may change or be omitted on alternate designs of the device.

The third general region 30 comprises an elongated arm that extends caudally and generally perpendicular to the second region, and is continuous with the second region 20. This third region 30 is folded down over the infant's lower extremities with sufficient length to tuck up under the infant's lower extremities to reach the infant's back, acting as a foot wrap portion, in a fashion that ensures that only a single layer of material is ever interspersed between the phototherapy lamp and the infant receiving phototherapy.

A means of affixing the distal end 32 of this region to the underside of the first region 12 or second region 14 may be included; said affixing means 34 is intended to provide the snugness required to swaddle an infant and further provides a boundary against which the infant's feet can push, an action that is recognized to further comfort the infant. In a preferred embodiment of the device, said affixing means 34 is a tab of Velcro-type hook material, although it is recognized that other means such as adhesive tapes may be used as well.

Alternatively, the swaddling blanket of the various embodiments of the invention may be effective without employing a means of affixing one portion of the blanket to another, relying instead on the infant's weight to maintain the snugness of the blanket.

In this first embodiment, the first general region 12 is intended to be disposed underneath the infant, such that in use the infant lies supine with his/her back resting over this region and head and feet oriented properly. The second general region 20 extends generally perpendicular to the first region 12 and is intended to wrap over and around the infant with sufficient length to reach the infant's back, but not long enough to wrap further around the infant. The center portion 22 of this second region 20 will lie generally atop the infant's torso when properly positioned, in a fashion that ensures that only a single layer of material is ever interspersed between the phototherapy lamp and the infant receiving phototherapy. The third general region 30 is then folded down over the infant's lower extremities with sufficient length to tuck up under the infant's lower extremities to reach the infant's back in a fashion that ensures that only a single layer of material is ever interspersed between the phototherapy lamp and the infant receiving phototherapy.

Figure 2:
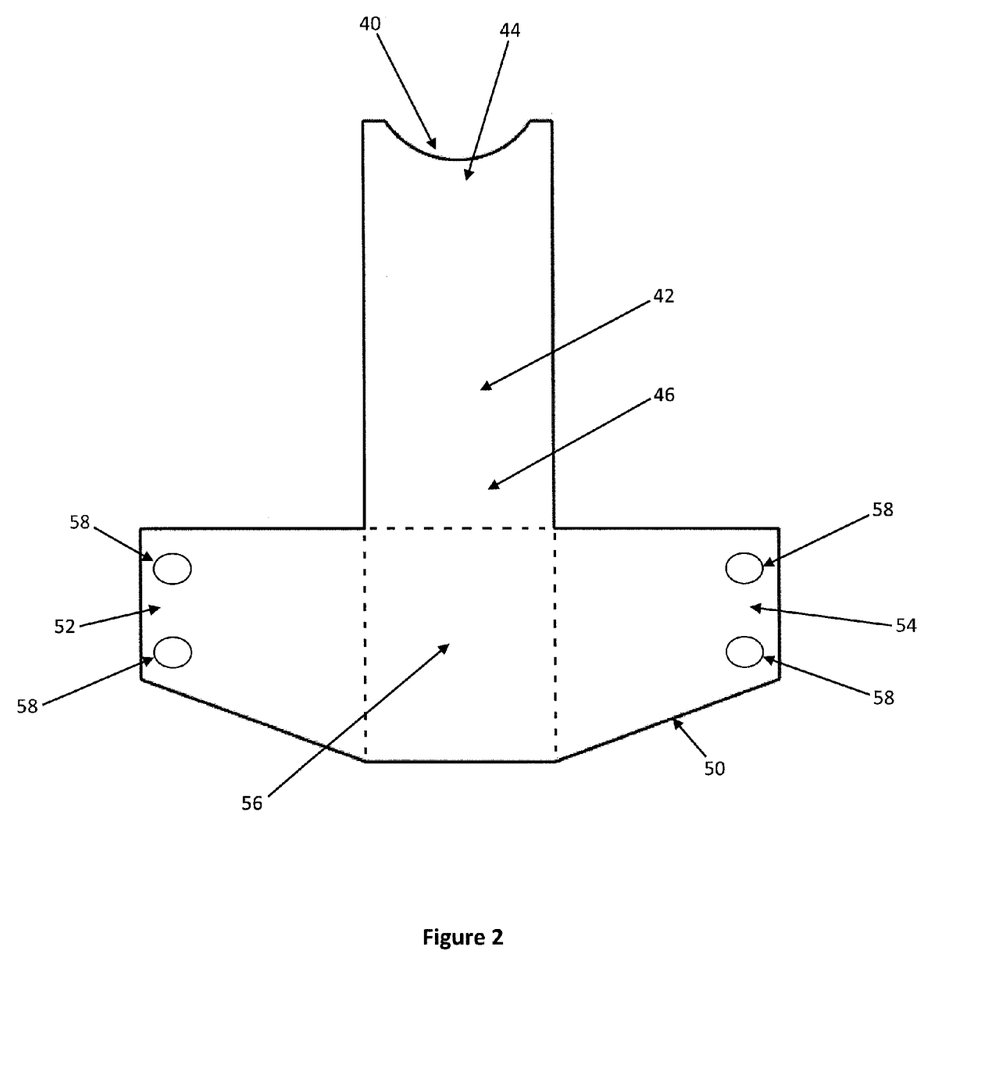
FIG. 2 is a plan view of a second embodiment of a phototherapy infant swaddling blanket in accordance with the invention.

In a second embodiment illustrated in FIG. 2, the swaddling blanket 40 has two general regions, said regions being continuous with each other. The first general region 42 is intended to be disposed behind the infant, having a head end 44 and a foot end 46, such that in use the infant lies supine with his/her back resting over this region with his/her head and feet oriented properly.

The second general region 50 is continuous with the first general region 42. It comprises an elongated section that is generally centered at the caudal or foot end 46 of the first region 42 and extends symmetrically in a generally perpendicular direction to the first general region 42. The distal ends 52, 54 of this second region 50 are intended to wrap over and around the infant with sufficient length to reach the infant's back, but not long enough to wrap further around the infant. The center portion 56 of this second region 50 will lie generally atop the infant's torso when properly positioned, in a fashion that ensures that only a single layer of material is ever interspersed between the phototherapy lamp and the infant receiving phototherapy.

A means of affixing the distal ends 52, 54 of this second region 50 to the underside of the first region 42 may be included; said affixing means 58 is intended to provide the snugness required to swaddle an infant without the need to wrap multiple times around the infant and interfere with the phototherapy energy delivered. In a preferred embodiment of the device, said affixing means 58 is a tab of Velcro-type hook material, although it is recognized that other means such as adhesive tapes may be used as well. Alternatively, as noted above, the swaddling blanket of the invention may be effective without employing a means of affixing one portion of the blanket to another, relying instead on the infant's weight to maintain the snugness of the blanket.

Figure 4:
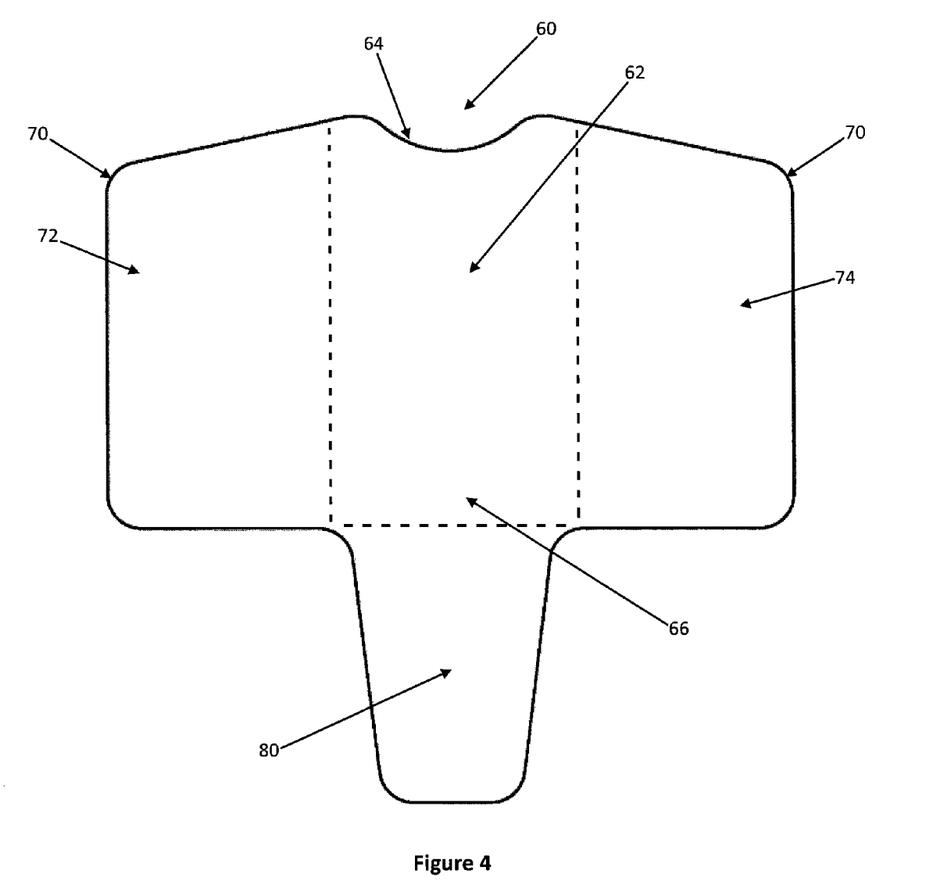
FIG. 4 is a plan view of a third embodiment of a phototherapy infant swaddling blanket in accordance with the invention.

In a third embodiment illustrated in FIG. 4, the swaddling blanket 60 has three general regions, said regions being contiguous with each other, providing a generally upright "T"-shaped configuration. The first general region 62 forms the leg of the "T" and is intended to be disposed over the torso and legs of the infant, having a head end 64 and a foot end 66, such that in use the infant lies supine and this region of the blanket is laid overtop the infant with his/her head and feet oriented properly. The head end 64 may include a scooped out region to indicate the preferred location for the infant's neck.

The second general region 70 is comprised of two "wings" or arms 72, 74 that make up the left and right sides of the first general region 62 and are contiguous with the first general region 62. In use, after the first general region 62 has been placed atop the infant, the two wings 72, 74 of the second general region 70 are folded down and under the infant's back in a fashion that snugly restrains the infant's arms against his/her sides, effectively swaddling the infant.

The third general region 80 is comprised of an elongated "tail" that arises from and is contiguous with the caudal or foot end 66 of the first general region 62. In use, after the first general region 62 has been placed atop the infant and the two "wings" 72, 74 of the second general region 70 have been folded down and under the infant's back, the "tail" or distal end of the third general region 80 is folded down and under the infant's legs and back. This forms a boundary against which the infant can push. Clinical research and observation has shown that such boundaries can enhance infant comfort and development.

The portions of the first, second and third general regions that lie atop the infant's torso when properly positioned ensure that only a single layer of material is ever interspersed between the phototherapy lamp and the infant receiving phototherapy. A means of affixing the distal ends 72, 74 of the second region 70 to each other, and the distal end of the third region 80 to the underside of the second region 70 may be included; said affixing means (not shown in this view) is intended to provide the snugness required to swaddle an infant without the need to wrap multiple times around the infant and interfere with the phototherapy energy delivered. In a preferred embodiment of the device 60, said affixing means is one or more tabs of Velcro-type hook material, although it is recognized that other means such as adhesive tapes may be used as well. Alternatively, the swaddling blanket of this embodiment may also be effective without employing a means of affixing one portion of the blanket to another, relying instead on the infant's weight to maintain the snugness of the blanket.

In a further aspect of the invention, a method of swaddling an infant undergoing a course of phototherapy is provided that ensures that there is ever only a single layer of swaddling material interspersed between the phototherapy lamp and the infant receiving phototherapy, and thus does not impede the delivery of the phototherapy. The method involves first taking a portion of material that is >45% light-transmissive, and preferably >90% light-transmissive, for light in the range of 350 nm to 500 nm wavelengths, then wrapping the infant in this portion of material in the specific steps of (1) first placing the infant in a supine position atop a portion of said material, then (2) wrapping a portion of said material over the infant and extending to the infant's back but not further around the infant, then (3) wrapping a portion of said material over the infant's lower extremities and extending to the infant's back but not further around the infant.

The current invention also describes an alternative method of swaddling an infant undergoing a course of phototherapy that ensures that there is ever only a single layer of swaddling material interspersed between the phototherapy lamp and the infant receiving phototherapy, and thus does not impede the delivery of the phototherapy. The method involves first taking a portion of material that is >45% light-transmissive, and preferably >90% light-transmissive, for light in the range of 350 nm to 500 nm wavelengths, then wrapping the infant in this portion of material in the specific steps of (1) first placing a portion of said material over top of an infant, then (2) wrapping a portion of said material over the infant and extending to the infant's back but not further around the infant, then (3) wrapping a portion of said material over the infant's lower extremities and extending to the infant's back but not further around the infant.

FIGS. 3a-3d illustrate a proposed folding scheme for the second embodiment of the invention. This folding scheme is used to ensure that only one layer of fabric material lies interspersed between the phototherapy lamp and the infant during the phototherapy treatment.

Figure 3A:
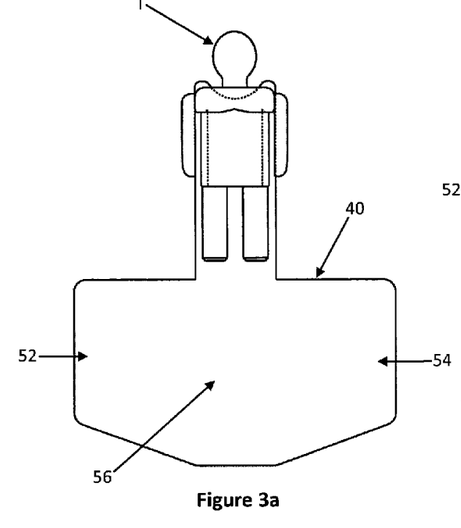
FIGS. 3a-3d are a series of schematic views illustrating the use of the swaddling blanket of FIG. 2.
Figure 3B:
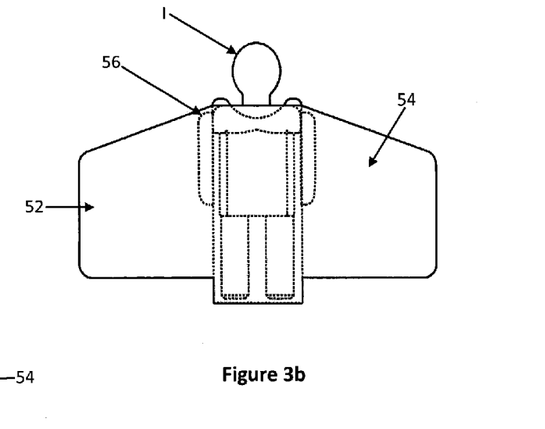
Figure 3C:
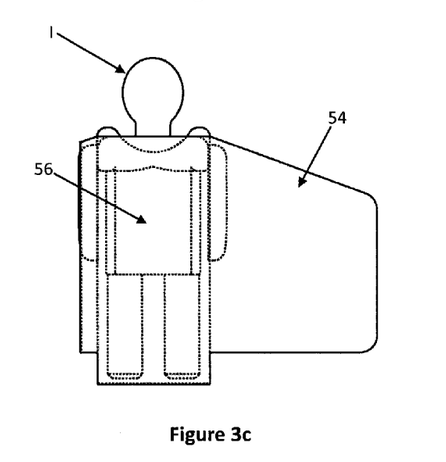
Figure 3D:
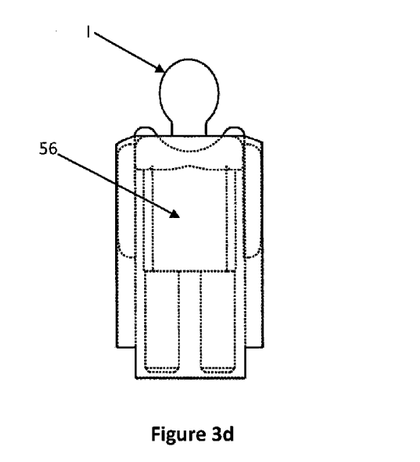

In FIG. 3a, the infant I is shown lying supine on the first region 42 of the open, unfolded blanket 40. In FIG. 3b, the second region 50 of the blanket 40 is shown with the center portion 56 folded up and over the infant I. FIG. 3c shows the end 52 of the second region 50 of the blanket 40 folded around behind or underneath the infant, and FIG. 3d shows both ends 52 and 54 folded around and behind the infant. The infant as shown in FIG. 3d is in the preferred swaddled position, with only one layer of material covering the front of the infant that is exposed to the phototherapy light. Affixing means are not shown in these views due to lack of space; it is understood that, if included, their location may be as depicted in FIG. 2.

FIGS. 5a-5d illustrate a proposed folding scheme for the third embodiment of the invention. This folding scheme ensures that only ever one layer of fabric material lies interspersed between the phototherapy lamp and the infant receiving phototherapy.

Figure 5A:
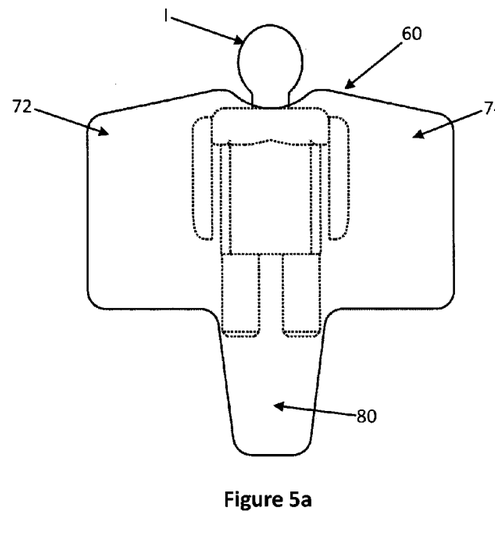
FIGS. 5a-5d are a series of schematic views illustrating the use of the swaddling blanket of FIG. 4.
Figure 5B:
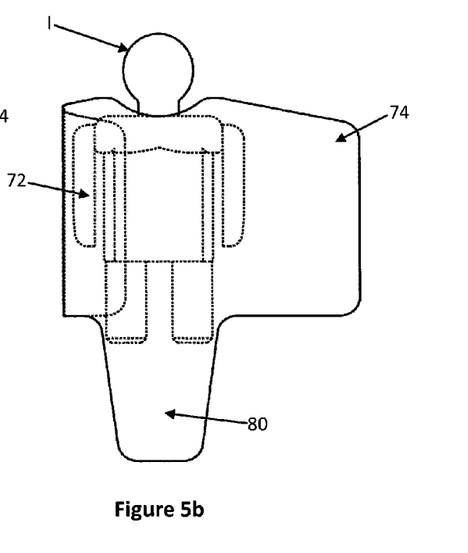
Figure 5C:
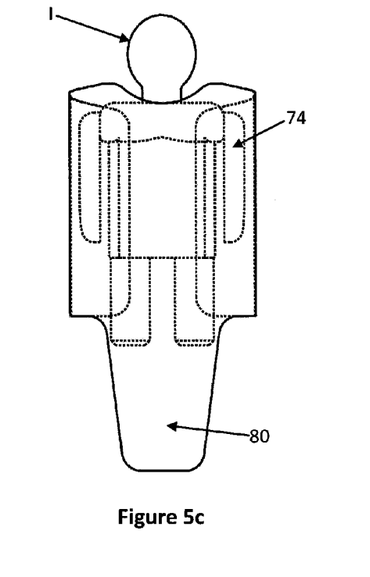
Figure 5D:
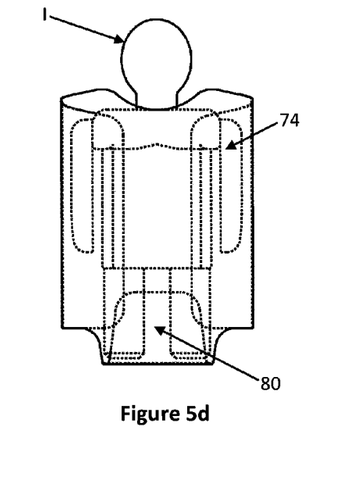

In FIG. 5a, the infant I is shown lying supine, with the open, unfolded blanket lying overtopping the infant. In the second panel, the first of the two blanket arms is shown folded around behind the infant. The third panel shows both blanket arms folded around behind the infant, and the fourth panel shows the "tail" folded under and behind the infant. The infant as shown in the fourth panel is in the preferred swaddled position, arms and legs snugly restrained, with only one layer of material covering the front of the infant that is exposed to the phototherapy light.

In accordance with the provisions of the patent statutes, the invention has been described in what is considered to represent its preferred embodiments. However, it should be noted that the invention could be practiced otherwise than as specifically illustrated and described without departing from its spirit or scope. As an example, it will be appreciated that, in those embodiments in which the apparatus includes a plurality of projections, the size and shape of the projections may vary considerably.

What is claimed is:

1. A method of swaddling an infant undergoing a course of phototherapy comprising:
   providing a sheet of fabric material of generally T-shaped configuration having a base region extending perpendicularly from a central portion of a cross region, the sheet of fabric material being >45% light-transmissive for light having a wavelength in the range of 350 nm to 500 nm; and
   folding the sheet of fabric material about the infant so that the infant is snugly wrapped in the sheet of fabric material, the sheet of fabric material limiting arm and leg movement of the infant, with only a single layer of the sheet of fabric material being located between a phototherapy lamp and the infant when the phototherapy lamp is placed above the infant.

2. The method of claim 1, wherein the fabric material is >90% light-transmissive for light having a wavelength in the range of 350 nm to 500 nm.

3. The method of claim 1, wherein the cross region includes a first distal end and a second distal end, one on either side of the central portion of the cross region, and the method further comprises:
   positioning the infant on top of the second distal end of the cross region;
   wrapping the first distal end of the cross region around the infant in the direction of the second distal end until the first distal end is underneath the infant and the central portion of the cross region lies atop the infant's torso; and
   wrapping a distal end of the base region underneath the infant in the direction of the head until the distal end of the base region is underneath the infant.

4. The method of claim 1, wherein the cross region includes a first distal end and a second distal end, one on either side of the central portion of the cross region, and the method further comprises:
   positioning the infant on top of the base region of the swaddling blanket with the infant's head at the distal end of the base region and the infant's feet at the proximal end of the base region;
   folding the cross region up over the infant such that the central portion of the cross region lies atop the torso of the infant;
   wrapping either the first or the second distal end of the cross region around the infant until such distal end is underneath the infant; and
   wrapping the other of the first or second distal ends of the cross region around the infant until such distal end is underneath the infant.

5. The method of claim 1, wherein the cross region includes a first distal end and a second distal end, one on either side of the central portion of the cross region, and the method further comprises:
   positioning the sheet of fabric material over the infant so that the central portion of the cross region lies atop the torso of the infant with the infant's feet proximate the base region;
   wrapping either the first or the second distal end of the cross region around the infant until such distal end is underneath the infant;
   wrapping the other of the first or second distal ends of the cross region around the infant until such distal end is underneath the infant; and wrapping a distal end of the base region underneath the infant in the direction of the head until the distal end of the base region is underneath the infant.

6. The method of claim 1, further comprising directing light having wavelengths in the range of 350 nm to 500 nm through only the single layer of the sheet of fabric material into contact with the infant.

7. The method of claim 1, further comprising utilizing one or more tabs of hook and loop material to affix one portion of the sheet of fabric material to another portion of the sheet of fabric material when the infant is snugly wrapped in the sheet of fabric material.

\* \* \* \* \*